US00PP28495P3

(12) United States Plant Patent
Klemm et al.

(10) Patent No.: US PP28,495 P3
(45) Date of Patent: Oct. 3, 2017

(54) ***BIDENS* PLANT NAMED 'KLEBF14326'**

(50) Latin Name: *Bidens ferulifolia*
Varietal Denomination: KLEBF14326

(71) Applicant: Klemm+Sohn GmbH & Co. KG, Stuttgart (DE)

(72) Inventors: Nils Klemm, Stuttgart (DE); Guido von Tubeuf, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 14/545,978

(22) Filed: Jul. 13, 2015

(65) Prior Publication Data
US 2017/0020054 P1 Jan. 19, 2017

(51) Int. Cl.
*A01H 5/02* (2006.01)

(52) U.S. Cl.
USPC ..... Plt./410

(58) Field of Classification Search
USPC ..... Plt./410
See application file for complete search history.

*Primary Examiner* — Keith Robinson
(74) *Attorney, Agent, or Firm* — Bethany R. Roahrig; James M. Weatherly; Cochran Freund & Young, LLC

(57) ABSTRACT

A new *bidens* plant particularly distinguished by having yellow colored flowers and a semi-upright plant habit, is disclosed.

1 Drawing Sheet

Genus and species: *Bidens ferulifolia.*
Variety denomination: 'KLEBF14326'.

BACKGROUND OF THE NEW PLANT

The present invention comprises a new and distinct variety of *bidens*, botanically known as *Bidens ferulifolia*, and hereinafter referred to by the variety name 'KLEBF14326'. 'KLEBF14326' originated from an open pollination between the proprietary female *bidens* variety 'BF-2010-0025' (unpatented) and an unknown male *bidens* variety.

In July 2011, two *bidens* parental lines, the female *bidens* variety 'BF-2010-0025' and an unkown male *bidens* variety were open pollinated in Stuttgart, Germany and seeds were obtained. The seeds were sown and plants were grown for evaluation. A plant line was selected in May 2012 which had yellow colored flowers and was subsequently named 'KLEBF14326'. In May 2012, 'KLEBF14326' was first vegetatively propagated by vegetative cuttings in Stuttgart, Germany. 'KLEBF14326' was found to reproduce true to type in successive generations of asexual propagation via vegetative cuttings.

SUMMARY

The following are the most outstanding and distinguishing characteristics of this new variety when grown under normal horticultural practices in Stuttgart Germany.

1. Yellow colored flowers; and
2. A semi-upright plant habit.

CROSS REFERENCE TO RELATED APPLICATIONS

Plant Breeder's Rights for 'KLEBF14326' were applied for in Canada on Apr. 2, 2015

(Application number 15-8562). 'KLEBF14326' has not been made publicly available or sold more than one year prior to the filing date of this application.

DESCRIPTION OF THE PHOTOGRAPH

This new *bidens* plant is illustrated by the accompanying photograph which shows the flowers and foliage of the plant grown in a pot. The photograph is of a five-month-old plant (grown 3 months in a greenhouse and 2 months outdoors) in Stuttgart, Germany in July 2013. The colors shown are as true as can be reasonably obtained by conventional photographic procedures.

DESCRIPTION OF THE NEW VARIETY

The following detailed descriptions set forth the distinctive characteristics of 'KLEBF14326'. The data which define these characteristics were collected from asexual reproductions carried out in Stuttgart, Germany. Data was collected on four-month-old plants grown outdoors in Stuttgart, Germany in May 2015. Color references are to The R.H.S. Colour Chart of The Royal Horticultural Society of London (R.H.S.), $5^{th}$ edition (2007).

Classification:
- *Family.*—Asteraceae.
- *Species.*—*Bidens ferulifolia.*
- *Variety.*—'KLEBF14326'.

Parentage:
- *Female.*—Proprietary female *bidens* 'BF-2010-0025' (unpatented).
- *Male.*—Proprietary male *bidens* unknown.

Plant description:
- *Habit.*—Semi-upright.
- *Height.*—12.0 cm.
- *Spread.*—10.0 cm.
- *Life cycle.*—Annual.
- *Form.*—Round to flat.

*Time to produce a rooted cutting.*—4 weeks.
*Root description.*—Fine, white, RHS NN155C.
*Rooting habit.*—Freely branching.
*Time to bloom from propagation.*—7 to 8 weeks after potting.
*Branching habit.*—Freely branching.

Lateral branches:
*Quantity.*—6 to 8.
*Color.*—RHS 144B.
*Pubescence.*—Absent.
*Diameter.*—0.2 cm.
*Length.*—3.0 cm to 5.0 cm.
*Internode length.*—1.0 cm to 2.0 cm.
*Anthocyanin.*—Present; RHS N77A.
*Strength.*—Medium.

Leaves:
*Arrangement.*—Opposite.
*Length.*—2.5 cm to 3.5 cm.
*Width.*—3.5 cm to 4.0 cm.
*Shape.*—Roughly elliptic and pinnatisect.
*Apex.*—Obtuse.
*Base.*—Acute.
*Margin.*—Pinnate.
*Texture* (*both surfaces*).—Smooth.
*Venation pattern.*—Pinnate.
*Color of developing leaves* (*immature*).—Upper surface: RHS 143A. Lower surface: RHS 143C. Venation color: Upper surface: RHS 144C. Lower surface: Closest to RHS 143A.
*Color of fully expanded leaves* (*mature*).—Upper surface: RHS 138A. Lower surface: RHS 138B. Venation color: Upper surface: RHS 144C. Lower surface: Closest to RHS 143C.
*Petiole.*—Length: 0.5 cm. Diameter: 0.1 cm. Color: RHS 144B with stripes of RHS N77A. Texture: Pubescent.

Inflorescence:
*Appearance.*—Daisy-type.
*Flowering habit.*—Continuously.
*Lastingness of inflorescence on the plant.*—5 to 6 days.
*Number of inflorescences and buds per plant.*—5 inflorescences and 3 to 5 buds at maturity.
*Fragrance.*—Present under sunlight, honey-like fragrance.
*Natural flowering season.*—Spring and summer.
*Diameter.*—4.5 cm.
*Depth.*—0.7 cm.
*Disc diameter.*—0.8 cm.

Flower buds:
*Length.*—0.5 cm.
*Diameter.*—0.5 cm to 0.6 cm.
*Surface texture.*—Smooth.
*Shape.*—Globular.
*Color.*—RHS 152A with stripes of RHS N144A.

Ray florets:
*Quantity per inflorescence.*—8.
*Length.*—2.2 cm.
*Width.*—1.2 cm.
*Shape.*—Ovate.
*Apex.*—Tridentate.
*Base.*—Acute.
*Margin.*—Entire.
*Color, when opening.*—Upper surface: RHS 9A. Lower surface: RHS 9B.
*Color, when fully open.*—Upper surface: RHS 9A. Lower surface: Closest to RHS 9B.
*Surface texture* (*both surfaces*).—Smooth.

Disc florets:
*Quantity per inflorescence.*—Approximately 80.
*Length.*—0.6 cm.
*Width.*—0.1 cm.
*Shape.*—Tubular.
*Apex.*—Five-pointed.
*Base.*—Fused.
*Margin.*—Entire.
*Color, when fully open.*—Upper surface: RHS 9A. Lower surface: RHS 4B.
*Surface texture* (*both surfaces*).—Smooth.

Phyllaries:
*Quantity per inflorescence.*—8 (plus calyx, 10).
*Length.*—0.6 cm.
*Width.*—0.15 cm.
*Shape.*—Lanceolate.
*Apex.*—Acute.
*Base.*—Truncate.
*Margin.*—Entire.
*Surface texture* (*both surfaces*).—Smooth.
*Color* (*both surfaces*).—RHS 152A.

Calyx:
*Length.*—0.5 cm.
*Width.*—0.15 cm.
*Shape.*—Lanceolate.
*Apex.*—Obtuse.
*Base.*—Truncate and fused.
*Margin.*—Entire.
*Surface texture.*—Upper surface: Smooth. Lower surface: smooth; Pubescent where fused.
*Color* (*both surfaces*).—RHS 137A.
*Receptacle.*—Diameter: 0.5 cm. Height: 0.2 cm. Color: Close to RHS 145B.

Peduncle:
*Length.*—1.5 cm to 2.5 cm.
*Diameter.*—0.15 cm.
*Color.*—RHS 146A.
*Texture.*—Smooth.
*Aspect.*—Round.
*Strength.*—Weak.

Reproductive organs:
*Androecium.*—Present on disc florets only. Quantity of stamens per floret: 5. Filament length: 1.0 cm. Filament color: Greyish-greenish yellow; close to RHS 150D. Anther length: 0.1 cm to 0.15 cm. Anther color: Dark brown; close to RHS 200A. Pollen amount: Sparse. Pollen color: RHS 14A.
*Gynoecium.*—Present on disc florets only. Quantity of pistils per floret: 1. Pistil length: 0.4 cm. Style length: 0.25 cm. Style color: Greyish-greenish yellow; close to RHS 150D. Stigma color: RHS 5A. Ovary color: RHS 142D.

Fruit/seed set: None observed.
Disease/insect resistance: None observed.

COMPARISON WITH PARENTAL LINES AND KNOWN VARIETY

'KLEBF14326' is a distinct variety of *bidens* and is distinguished from its female parent as described in Table 1:

TABLE 1

| Comparison with Parental Line | | |
|---|---|---|
| Trait | Variety 'KLEBF14326' | Female Parent 'BF-2010-0025' |
| Vigor | Less compact than 'BF-2010-0025' | More compact than 'KLEBF14326' |
| Branching | More branching than 'BF-2010-0025' | Less branching than 'KLEBF14326' |

'KLEBF14326' is most similar to the commercial line *bidens* plant named 'Tweety Compact 2015' (unpatented). Differences between the two varieties are described in Table 2:

TABLE 2

| Comparison with Similar Variety | | |
|---|---|---|
| Trait | Variety 'KLEBF14326' | Commercial line 'Tweety Compact 2015' |
| Ray floret color | Lighter yellow than 'Tweety Compact 2015' | Deeper yellow than 'KLEBF14326' |
| Petioles | Stripes of N77A on green background (RHS 144 B) | Almost whole surface N77A |
| Calyx leaflets | Longer than 'Tweety Compact 2015' | Shorter than 'KLEBF14326' |

We claim:

1. A new and distinct variety of *bidens* plant named 'KLEBF14326' as illustrated and described herein.

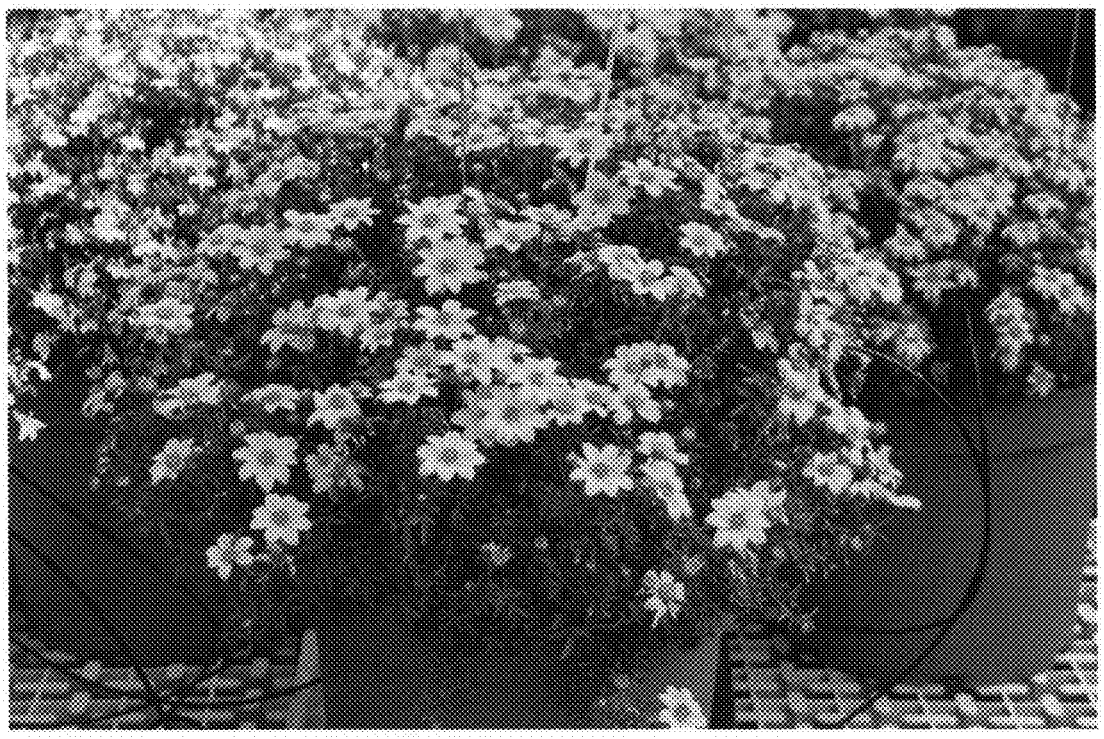

* * * * *